(12) United States Patent
Gelbart et al.

(10) Patent No.: US 7,267,751 B2
(45) Date of Patent: Sep. 11, 2007

(54) PROGRAMMABLE MULTIPLEXED ACTIVE BIOLOGIC ARRAY

(75) Inventors: Richard Gelbart, San Diego, CA (US);
Don L. Powrie, San Diego, CA (US);
Paul David Swanson, Santee, CA (US)

(73) Assignee: Nanogen, Inc., San Diego, CA (US)

( * ) Notice: Subject to any disclaimer, the term of this patent is extended or adjusted under 35 U.S.C. 154(b) by 0 days.

(21) Appl. No.: 10/224,750

(22) Filed: Aug. 20, 2002

(65) Prior Publication Data

US 2004/0038420 A1 Feb. 26, 2004

(51) Int. Cl.
*G01N 27/27* (2006.01)
*G01N 27/26* (2006.01)
*G01N 27/327* (2006.01)
*G01N 27/453* (2006.01)
*G01N 15/06* (2006.01)

(52) U.S. Cl. .................. 204/406; 422/50; 422/61; 422/68.1; 422/81; 422/82.01; 422/82.02; 436/43; 436/63; 436/149; 436/150; 436/151; 204/193; 204/400; 204/403.01; 204/403.03; 204/403.13; 204/407; 204/409; 204/411; 204/412

(58) Field of Classification Search .................. 422/50, 422/61, 68.1, 81, 82.01, 82.02; 436/43, 63, 436/149, 150, 151; 204/193, 400, 403.01, 204/403.03, 403.13, 406, 407, 409, 411, 412
See application file for complete search history.

(56) References Cited

U.S. PATENT DOCUMENTS

| | | | |
|---|---|---|---|
| 3,430,072 A | 2/1969 | Stevens | |
| 3,957,592 A | 5/1976 | Young | |
| 4,594,135 A | 6/1986 | Goldstein | |
| 4,661,224 A | 4/1987 | Goldstein et al. | |
| 4,772,851 A | 9/1988 | Schattschneider | |
| 4,787,963 A | 11/1988 | MacConnell | |
| 4,924,224 A | 5/1990 | Takahasi et al. | |
| 5,074,977 A | 12/1991 | Cheung et al. | |
| 5,164,319 A | 11/1992 | Hafeman et al. | |
| 5,178,161 A | 1/1993 | Kovacs | |
| 5,187,096 A | 2/1993 | Giaever et al. | |
| 5,234,566 A | 8/1993 | Osman et al. | |

(Continued)

FOREIGN PATENT DOCUMENTS

EP 0376611 A2 7/1990

(Continued)

OTHER PUBLICATIONS

Fiaccabrino et al, "Array Of Individually Addressable Microelectrodes", Sensors & Actuators B, 16-19, 1994, 675-677.

*Primary Examiner*—Brian Sines
(74) *Attorney, Agent, or Firm*—O'Melveny & Myers LLP (57) ABSTRACT

The present invention is directed to devices and methods for carrying out and/or monitoring biological reactions in response to electrical stimuli. A programmable multiplexed active biologic array includes an array of electrodes coupled to sample-and-hold circuits. The programmable multiplexed active biologic array includes a digital interface that allows external control of the array using an external processor. The circuit may monitor, digitally control, and deliver electrical stimuli to the electrodes individually or in selected groups.

22 Claims, 8 Drawing Sheets

U.S. PATENT DOCUMENTS

| | | |
|---|---|---|
| 5,314,495 A | 5/1994 | Kovacs |
| 5,378,343 A | 1/1995 | Kounaves et al. |
| 5,434,049 A | 7/1995 | Okano et al. |
| 5,445,934 A | 8/1995 | Fodor et al. |
| 5,491,097 A | 2/1996 | Ribi et al. |
| 5,527,670 A | 6/1996 | Stanley |
| 5,605,662 A | 2/1997 | Heller et al. |
| 5,632,876 A | 5/1997 | Zanzucchi et al. |
| 5,632,957 A | 5/1997 | Heller et al. |
| 5,653,939 A | 8/1997 | Hollis et al. |
| 5,770,721 A | 6/1998 | Ershov et al. |
| 5,849,486 A | 12/1998 | Heller et al. |
| 5,851,772 A | 12/1998 | Mirzabekov et al. |
| 5,861,247 A | 1/1999 | Mirzabekov et al. |
| 5,891,630 A | 4/1999 | Eggers et al. |
| 5,905,024 A | 5/1999 | Mirzabekov et al. |
| 5,965,452 A | 10/1999 | Kovacs |
| 5,981,268 A * | 11/1999 | Kovacs et al. ............ 435/287.1 |
| 6,017,696 A | 1/2000 | Heller |
| 6,048,690 A | 4/2000 | Heller et al. |
| 6,051,380 A | 4/2000 | Sosnowski et al. |
| 6,054,270 A | 4/2000 | Southern |
| 6,068,818 A | 5/2000 | Ackley et al. |
| 6,093,302 A | 7/2000 | Montgomery |
| 6,099,803 A | 8/2000 | Ackley et al. |
| 6,258,606 B1 * | 7/2001 | Kovacs ........................ 436/149 |
| 6,602,400 B1 * | 8/2003 | Choong et al. .......... 205/777.5 |
| 6,682,936 B2 * | 1/2004 | Kovacs ........................ 436/149 |
| 6,726,820 B1 * | 4/2004 | Frazier ........................ 204/451 |
| 2001/0036641 A1 | 11/2001 | Gordon et al. |
| 2002/0008038 A1 | 1/2002 | Heller et al. |

FOREIGN PATENT DOCUMENTS

| | | |
|---|---|---|
| WO | WO93/22678 A2 | 11/1993 |
| WO | WO95/12808 A1 | 5/1995 |
| WO | WO99/67019 A1 | 12/1999 |

* cited by examiner

PROGRAMMABLE MULTIPLEXED ACTIVE BIOLOGIC ARRAY

FIELD OF THE INVENTION

The field of the invention relates generally to devices and methods for carrying out and/or monitoring biologic reactions in the presence of electrical stimuli. More specifically, the present invention relates to the design, implementation, and use of an array-based electronic system for carrying out and/or monitoring biologic reactions in response to electrical stimuli.

BACKGROUND OF THE INVENTION

For some time now, substantial attention has been directed to the design, implementation and use of array-based electronic systems for carrying out and/or monitoring biologic reactions.

Figure 1:
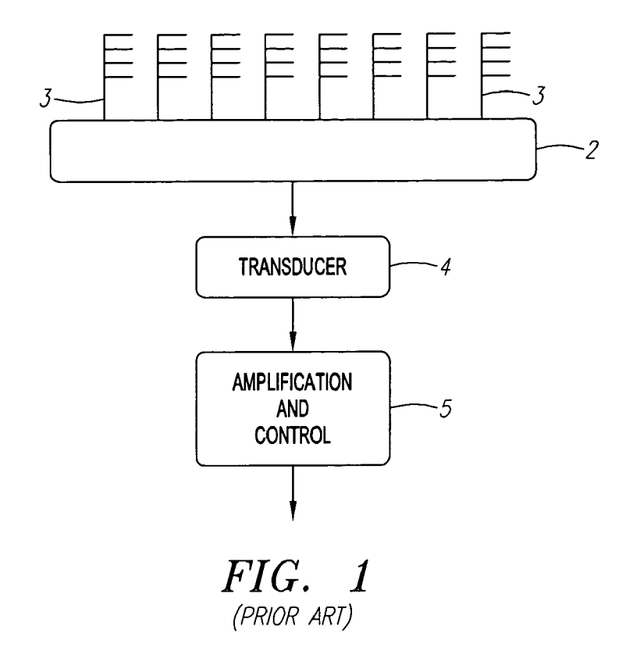
FIG. 1 is an illustration of a prior art passive biologic system.

For example, it has been recognized that electronic biosensors of various types may be used to monitor (or measure) the progress of certain biologic reactions, and that arrays of these sensors may be fabricated using techniques similar to those utilized in the integrated circuits field. As shown in FIG. 1, a typical prior art biosensor 1 may include a biospecific immobilization surface 2 having an immobilized affinity ligand 3 bound thereto, a transducer 4 capable of sensing the occurrence of chemical reactions which may occur between the immobilized ligand 3 and a specific analyte, and an amplification and control unit 5 for filtering, amplifying and translating signals generated by the transducer 4 into various measurements useful for monitoring the progress or occurrence of a selected biologic reaction. Biosensors of the type described above are discussed in some detail in Protein Immobilization, Fundamentals & Applications, R. F. Taylor, ed. (1991) (chapter 8); and Immobilized Affinity Ligand Techniques, Hermanson et al. (1992) (chapter 5).

The fabrication of an array of biosensors is disclosed, for example, in U.S. patent application Ser. No. 07/872,582, entitled "Optical and Electrical Methods and Apparatus for Molecule Detection" (published Nov. 14, 1993 as International Publication No. W093/22678, and hereinafter referred to as "the Hollis et al. application"). The Hollis et al. application is directed primarily to biosensory devices comprising an array of test sites which may be electronically addressed using a plurality of conductive leads. Various types of biosensors are described for use at the test sites, and it is suggested that the test sites may be formed in a semiconductor wafer using photolithographic processing techniques. It is further suggested that the test sites may be coupled to associated detection circuitry via transistor switches using row and column addressing techniques employed, for example, in addressing dynamic random access memory (DRAM) or active matrix liquid crystal display (AMLCD) devices.

Figure 2:
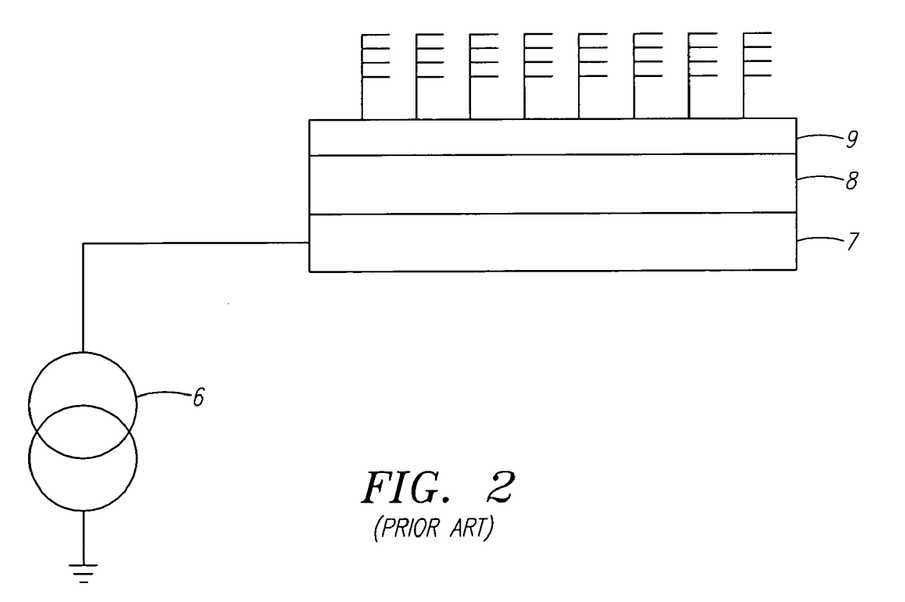
FIG. 2 is an illustration of a prior art active biologic system.

In addition to the biosensor devices described above, several devices capable of delivering an electrical stimulus (or signal) to a selected location (or test site) within a solution or elsewhere, have been developed. As shown in FIG. 2, these devices often include a source 6, such as a current, voltage or power source, an electrode 7 coupled to the current source 6, a permeation layer 8 formed on one surface of the electrode 7, and a biologic attachment layer 9 formed upon the permeation layer 8. The permeation layer 8 provides for free transport of small counter-ions between the electrode 7 and a solution (not shown), and the attachment layer 9 provides for coupling of specific binding entities.

Exemplary systems of the type described above are disclosed in PCT Application No. PCT/US94/12270, which was published in May 1995, and is entitled "Self-Addressable Self-Assembling Microelectronic Systems and Devices for Molecular Biological Analysis and Diagnostics," and PCT Application No. PCT/US95/08570, which was published on Jan. 26, 1996, and is entitled "Self-Addressable Self-Assembling Microelectronic Systems and Devices for Molecular Biological Application," (hereinafter "the Heller et al. applications") both of which are hereby incorporated by reference. The Heller et al. applications describe electronic devices which may be fabricated using microlithographic or micromachining techniques, and preferably include a matrix of addressable micro-locations on a surface thereof. Further, individual micro-locations are configured to electronically control and direct the transport and attachment of specific binding entities (e.g., nucleic acids, antibodies, etc.) to itself. Thus, the disclosed devices have the ability to actively carry out controlled multi-step and multiplex reactions in microscopic formats. Applicable reactions include, for example, nucleic acid hybridizations, antibody/antigen reactions, clinical diagnostics, and multi-step combinational biopolymer synthesis reactions.

Additional electronic systems for interfacing with various solutions and/or biologic entities are disclosed in European Patent Application No. 89-3133379.3, published Apr. 7, 1990 and entitled "Electrophoretic System;" U.S. Pat. No. 5,378,343, issued Jan. 3, 1995 and entitled "Electrode Assembly Including Iridium Based Mercury Ultramicroelectrode Array;" U.S. Pat. No. 5,314,495, issued May 24, 1995 and entitled "Microelectronic Interface;" and U.S. Pat. No. 5,178,161, issued Jan. 12, 1993 and entitled "Microelectronic Interface."

Those skilled in the art will appreciate, however, that conventional electronic systems for carrying out and/or monitoring biologic reactions (including the devices described in the above-referenced patents and patent applications) are often bulky, expensive and, at times, difficult to control. Moreover, those skilled in the art will appreciate that, because conventional biologic systems often utilize "off-chip" circuitry to generate and control the current/voltage signals which are applied to an array of test sites, it is often difficult without the use of special equipment to precisely control the current/voltage signals generated at particular test sites. As for those conventional systems which do employ "on-chip" circuitry to generate and control the current/voltage signals which are applied to an array of test sites, in certain cases substantial difficulties have been encountered where it is desired to provide separate and distinct stimuli to selected electrode sites within a large array. One reason for this is that, when single site stimulus specificity is desired within conventional biosensor arrays, that need is often satisfied through the provision of independent signal lines for each electrode site within the array. As a result, conventional biologic systems are often more cumbersome, unreliable, and expensive than is desirable.

In view of the above-noted limitations of conventional biologic systems, it is submitted that an improved biologic system which utilizes a minimum of "off-chip" circuitry and enables the use of large arrays of electrode sites while providing for precise control of the voltages/currents delivered at a given electrode site, would be both useful and desirable.

SUMMARY OF THE INVENTION

In a first aspect of the invention, a digitally programmable array-based electronic chip is employed for carrying out biological reactions in response to electrical stimuli. The chip includes an array of electrode sites. Each electrode site includes a sample-and-hold circuit coupled to a working electrode.

The chip further includes a plurality of switches for selectively coupling the working electrodes to the output of a digital-to-analog converter (DAC). In addition, a control logic module is coupled to the DAC and the plurality of switches. An external processor digitally interfaces with the control logic module, wherein the communication between the control logic module and the external processor includes a clock signal, a data in signal, and a data out signal.

In a second aspect of the invention, a method is employed for carrying out biological reactions in response to electrical stimuli applied to a plurality of electrodes. The method includes the step of providing a chip having an array of electrode sites, each electrode site containing a sample-and-hold circuit coupled to a working electrode, a digital-to-analog converter (DAC), a plurality of switches for selectively coupling the DAC to the sample-and-hold circuits, and a control logic module coupled to the DAC and the plurality of switches.

The method further includes the steps of providing an external processor that digitally interfaces with the chip and driving the working electrodes in accordance with the instructions contained in the external processor.

It is an object of the invention to provide an array-based electronic chip for carrying out biological reactions. The chip includes a digital interface that allows the chip to be controlled by an external processor such as, for example, a personal computer. Individual electrodes or groups of electrodes within the array can be precisely controlled using the external processor. The electrodes can be driven in a number of ways, including constant voltage, constant current, and voltage offset. The chip also includes measurement circuitry to monitor certain aspects of the chip such as, for example, electrode voltages, electrode currents, and temperature conditions of the chip.

Additional objects and advantages of the invention are described below.

BRIEF DESCRIPTION OF THE DRAWINGS

FIG. 5(*a*) is an illustration of an electrode site configured to operate in normal mode in accordance with a preferred embodiment of the present invention.

FIG. 5(*b*) is an illustration of an electrode site configured to operate in high-impedance mode in accordance with a preferred embodiment of the present invention.

FIG. 5(*c*) is an illustration of an electrode site configured to operate in current measurement mode in accordance with an embodiment of the present invention.

FIG. 5(*d*) is an illustration of an electrode site configured to operate in voltage measurement mode in accordance with an embodiment of the present invention.

FIG. 5(*e*) is an illustration of an electrode site configured to operate in current measurement mode in accordance with a preferred embodiment of the present invention.

FIG. 5(*f*) is an illustration of an electrode site configured to operate in voltage measurement mode in accordance with a preferred embodiment of the present invention.

FIG. 7(*a*) is an illustration of a frontal view of a cartridge in accordance with a preferred embodiment of the present invention.

FIG. 7(*b*) is an illustration of a back view of a cartridge in accordance with a preferred embodiment of the present invention.

DETAILED DESCRIPTION OF THE PREFERRED EMBODIMENTS

Figure 3:
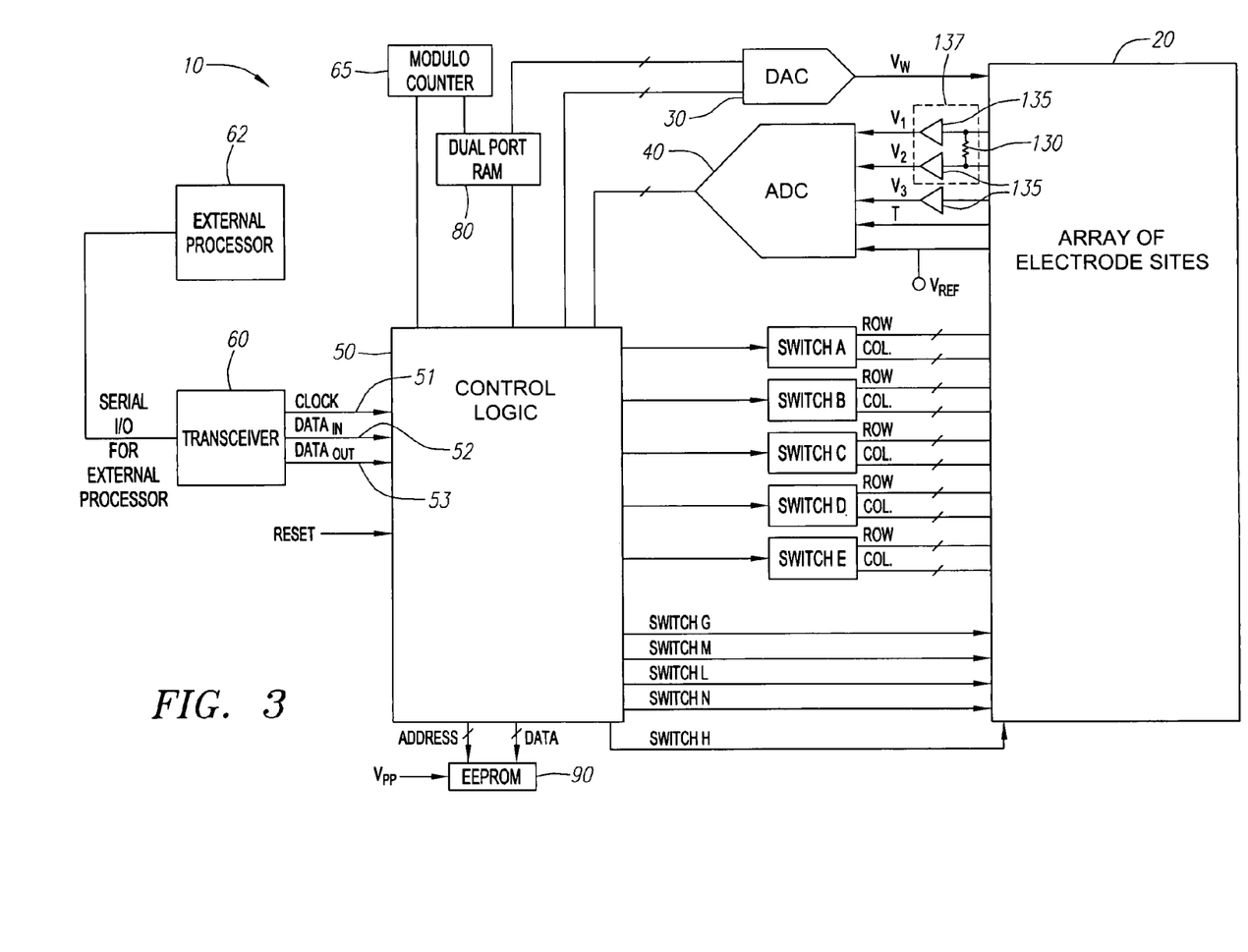
FIG. 3 is an illustration of an array-based circuit in accordance with a preferred embodiment of the present invention.

Turning now to the drawings, as shown in FIG. 3, an array-based electronic chip 10 for carrying out and/or monitoring biologic reactions in accordance with one preferred form of the present invention comprises an array 20 of active biologic electrode sites 100. Coupled to the array 20 are a digital-to-analog converter (DAC) 30, an analog-to-digital converter (ADC) 40, and a plurality of switch controls, A, B, C, D, E, G, M, L, N, and H.

The array-based chip 10 further includes a counter 65, e.g., a modulo 402 counter, a dual port random access memory module (RAM) 80, and an electrically eraseable programmable read only memory module (EEPROM) 90 coupled to a control logic module 50, which, in turn, is coupled to the DAC 30, the ADC 40, and switch controls (A-E, G, M, L, N, and H). In a preferred embodiment, each of the above listed elements may be disposed on a single semiconductor chip, and the entire chip 10 may be fabricated using conventional CMOS semiconductor fabrication techniques. Further details on the fabrication techniques, which may be employed in making the chip 10, are disclosed in U.S. Pat. No. 6,258,606 issued to Kovacs, which is hereby incorporated by reference in its entirety.

Further, in the presently preferred form, an external processor 62, such as a computer, may be used to interface with the chip 10. Preferably, the external processor 62 may communicate with the chip 10 serially, using a transceiver 60 that enables synchronous communication with the control logic module 50. The communication interface between the transceiver 60 and the control logic module 50 includes three signals: data-in 52, data-out 53, and a clock signal 51, which may come from the external processor 62.

Figure 4:
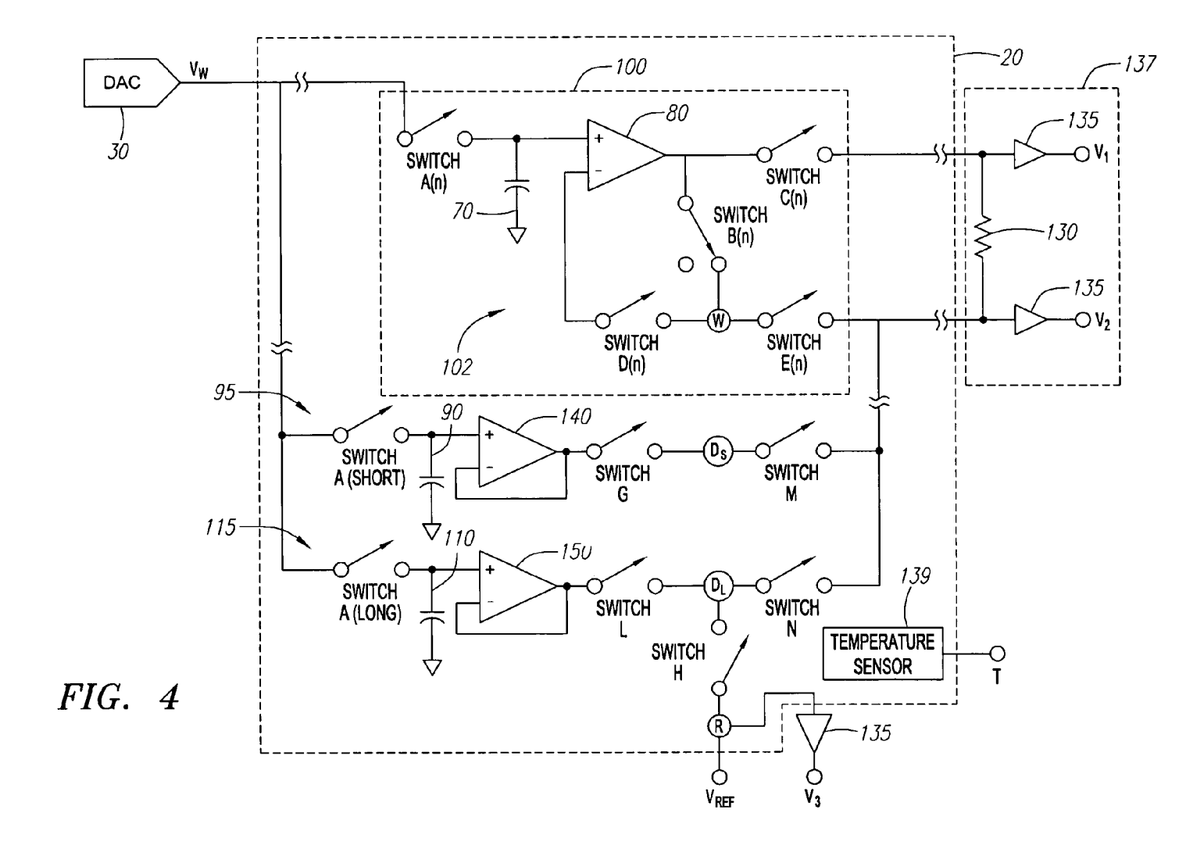
FIG. 4 is an illustration of an array of electrode sites in accordance with a preferred embodiment of the present invention.

Turning now to FIG. 4, the array 20 includes an array of individual biologic electrode sites 100. Each electrode site 100 includes a working electrode W coupled with a sample-and-hold circuit 102, which may include five switches, A(n), B(n), C(n), D(n), and E(n) (n identifies a particular electrode site 100) a capacitor 70, and an operational amplifier 80. The switch controls A, B, C, D, and E shown in FIG. 3 may be respectively coupled with each of switches A(n), B(n), C(n), D(n), an E(n) via row and column signal lines coupled to row and column decoders (not shown) to enable the switches to be controlled individually. Preferably, array 20 is further coupled with a measurement circuit 137 comprising an external resistor 130 and two nodes coupled with two voltage sense amplifiers 135 for voltage measurements, $V_1$ and $V_2$.

Still referring to FIG. 3, in addition to the array of biologic electrode sites 100, the array 20 may further include two dump circuits 95, 115, namely a short dump circuit 95 and a long dump circuit 115. The short dump circuit 95 preferably includes switches A(short), G, and M, a capacitor 90, an operational amplifier 140, and a short dump electrode $D_s$. The long dump circuit 115 may include switches A(long), L, and N, a capacitor 110, an operational amplifier 150, and a long dump electrode $D_1$. The short 95 and/or long dump circuits 115 may further be coupled with a reference electrode R, via a switch H (reference electrode R is shown in FIG. 3 only coupled to the long dump circuit 115). An external reference voltage source, $V_{ref}$, is preferably applied to the reference electrode R, which may also be coupled to a voltage sense amplifier 135 that provides a voltage measurement node, $V_3$. Switches G, M, L, N, and H may be controlled by the control logic module 50 shown in FIG. 3. The array 20 also preferably includes a temperature sensor 139, which provides a temperature measurement T of the solution containing biologic material.

Generally, each electrode site 100 and dump circuit 95, 115 operates in two states, a sample state and a hold state. When a particular electrode site (n) 100 or dump circuit 95, 115 is in a sample state, switch A(n, short, or long) closes, and the voltage, $V_w$, supplied by the DAC 30 is applied to the capacitor 70, 90, 110 until the capacitor 70, 90, 110 charges to a level that supplies a desired amount of voltage to the operational amplifier 80, 140, 150. Then, the electrode site (n) 100 or dump circuit 95, 115 changes to a hold state, where switch A(n, short, or long) opens, and the voltage applied to the noninverting input terminal(+)of the amplifier 80, 140, 150 is thus supplied by the capacitor 70, 90, 110. The capacitor 70, 90, 110 is preferably of a size, e.g., approximately 20 pF, that can quickly acquire the desired charge when switch A(n, short, or long) closes and hold the charge for a sufficient amount of time when switch A(n, short, or long) opens. As will be described below in more detail, during operation of the chip 10, the charge in each capacitor 70, 90, 110 is refreshed, i.e., recharged, preferably once approximately every 40.2 μsec.

Figure 5A:
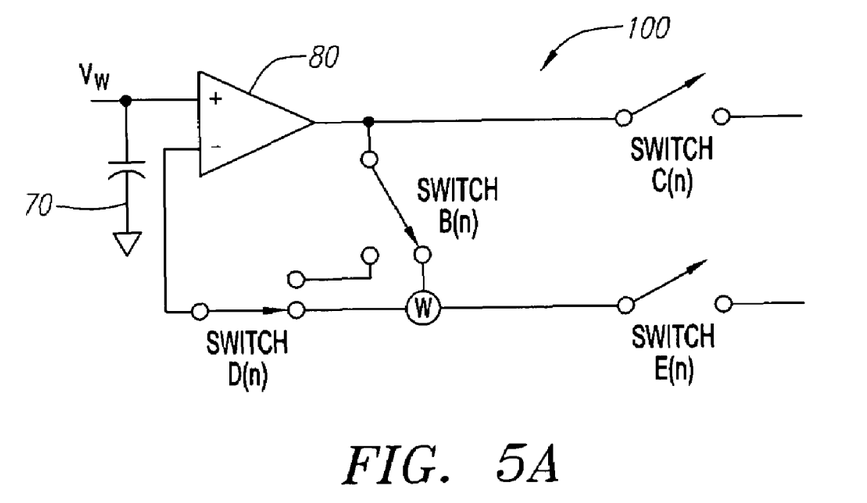

Additionally, the electrode sites 100 preferably operate in a variety of modes, e.g., normal mode, high-impedance mode, current measurement mode, and voltage measurement mode. Turning to FIG. 5(a), an electrode site 100 is setup to operate in normal mode, wherein a desired voltage is applied to the working electrode W. This mode is commonly referred to as "wet" mode because a solution is applied to the surface of the chip 10 containing the working electrodes W. Switches B(n) and D(n) form a closed circuit with the working electrode W, i.e., positioned such that the output of the operational amplifier 80 is applied to the working electrode W (i.e., to drive the working electrode W) and then fed back to inverting input terminal (−) of the operational amplifier 80. Switches C(n) and E(n) are open during normal mode.

Figure 5B:
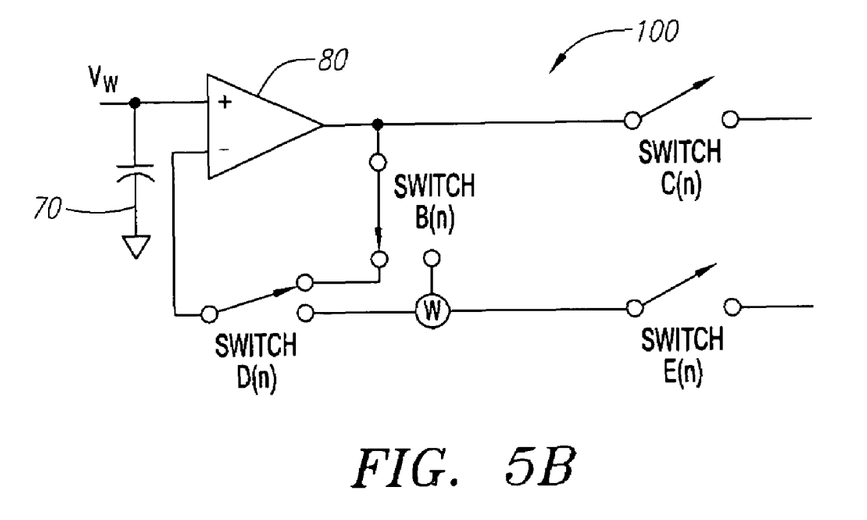

Turning to FIG. 5(b), the electrode site 100 is shown configured in high-impedance mode, which effectively isolates the working electrode W from the array 20. In this mode, switches B(n) and D(n) form open circuits with the working electrode W, i.e., positioned such that the output of the operational amplifier 80 bypasses the working electrode W. Switches C(n) and E(n) are open during high-impedance mode.

Figure 5C:
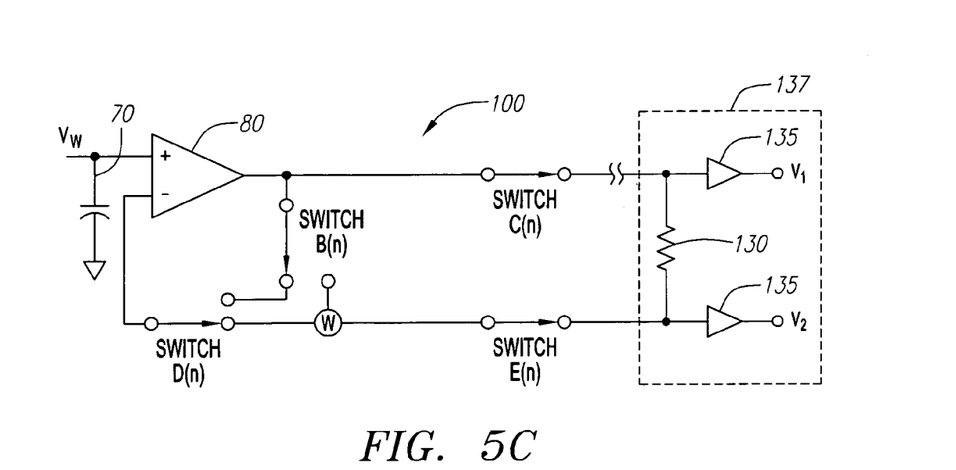

Turning to FIG. 5(c), the electrode site 100 is configured in current measurement mode, wherein the current through the working electrode W may be measured. Switch B(n) forms an open circuit with the working electrode W. Switch D(n) forms a closed circuit with the working electrode W. Both switches C(n) and E(n) are closed, creating a circuit loop with the measurement circuit 137, i.e., a circuit loop is created through the external resistor 130, which is preferably a precision resistor, the working electrode W, and the operational amplifier 80. The current through the working electrode W may be calculated by subtracting $V_1$ from $V_2$, the outputs of the voltage sense amplifiers 135, and dividing the difference by the external resistor 130 in accordance with Ohm's law, i.e., $(V_1-V_2)/(\text{Resistor } 130)$. The resistor 130 is preferably approximately 385 kΩ.

Figure 5D:
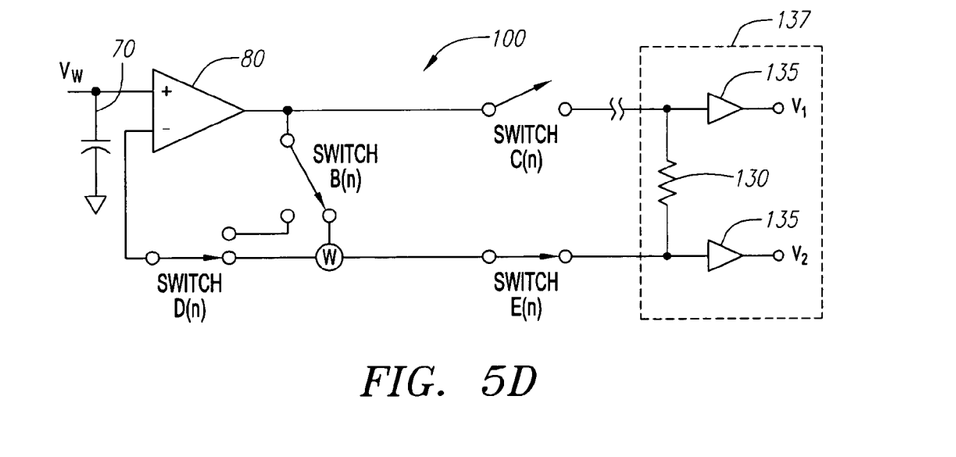

Turning to FIG. 5(d), the electrode site 100 is set up in voltage measurement mode, wherein the voltage applied to the working electrode W may be measured and tested. The configuration is similar to normal mode shown in FIG. 5(a), except that switch E(n) is closed. Thus, the voltage applied at the working electrode W can be measured at $V_2$. In addition to being able to measure the working electrode W voltage $V_2$ with solution applied, this mode of operation also allows dry test capability, i.e., the electrodes W, D and R may be tested before a solution is placed over the array 20. In this regard, the integrity of the chip 10 can be tested at the manufacturing facility much earlier in the manufacturing process than prior devices.

Figure 5E:
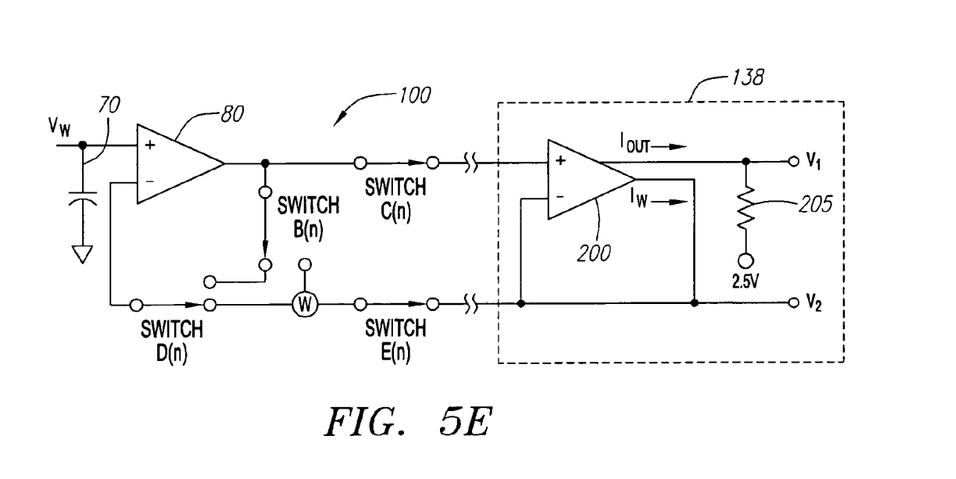

Turning to FIG. 5(e), the electrode site 100 is configured in current measurement mode coupled with an alternative measurement circuit 138, which includes a transconductance amplifier 200. The noninverting input terminal (+) of the amplifier 200 is coupled with switch C(n), which is closed. The inverting input terminal (−) and the output of the amplifier 200 are coupled with switch E(n), which is also closed.

The amplifier 200 outputs a current, $I_w$, which represents the current through the working electrode W. However, $I_w$ may include parasitic noise caused by the sample-and-hold circuits of the electrode sites 100. Because the amplifier 200 outputs a current, the impedance of the amplifier 200 is high, which, as can be appreciated by one of ordinary skill in the art, allows the output current to be accurately copied with reduced parasitic noise. Thus, to reduce the parasitic noise of $I_w$, the amplifier 200 produces a copied version $I_{out}$, $I_{out}$ is passed through a resistor 205, which may be coupled with a ground or an external voltage source, e.g., a voltage source $V_{ref}$ of 2.5V. In accordance with Ohm's law, the current $I_w$ may be calculated by subtracting $V_1$ by the voltage source, e.g., a $V_{ref}$ of 2.5V, and dividing the difference by the value of the resistor 205. The resistor 205 is preferably approximately 385 kΩ.

Figure 5F:
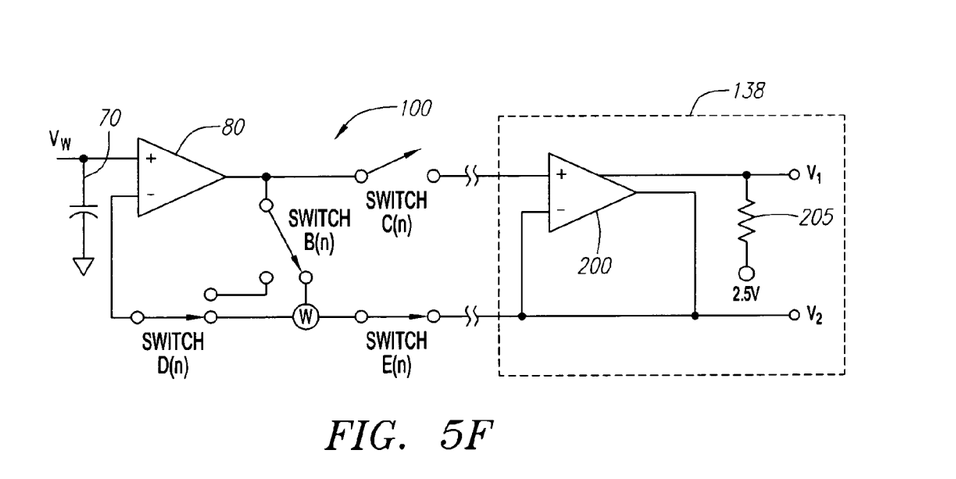

Turning to FIG. 5(f), an electrode site 100 is shown coupled with measurement circuit 138. The electrode site 100 is configured in voltage measurement mode, wherein the voltage of the working electrode W may be measured. The configuration is similar to the configuration of the normal mode, as shown in FIG. 5(a), except that switch E(n) is closed, thus closing the circuit with the node at $V_2$. The voltage at $V_2$ represents the voltage of the working electrode W.

As mentioned above, in addition to the array of electrode sites 100, the array 20 may include dump circuits 95, 115, such as the short dump circuit 95 and long dump circuit 115 shown in FIG. 4. During operation of the sample-and-hold circuits of the electrode sites 100, there are some situations where it may be desirable to have a reference node shorted to ground. In other situations, it may be desirable to maintain a reference node at a voltage level other than ground. In these other situations, one approach is to couple the reference node to a dump circuit having a potential other than ground.

One possible situation, for example, is when measuring the current of the working electrode W using the current measurement circuit 138, described above and shown in FIG. 5(e). During operation, the voltage $V_1$ may switch between a first and second value. If the resistor 205 was coupled to a reference node that was shorted to ground, then the measured current, i.e., $V_1$ divided by the resistor 205, may oscillate between a higher current and a lower current. If the reference mode was set to a voltage approximately in between the first and second value, then the measured voltage $V_1$ of the electrode may switch between a negative value and a positive value, which in turn results in a current measurement that switches between a negative value and a positive value.

As can be appreciated by one of ordinary skill in the art, this advantageously allows the working electrodes W to function as "counter-electrodes" for each other. In other words, if the current of a working electrode W is flowing in one direction, e.g., a positive current, a circuit may be completed by coupling the working electrode W with another working electrode W having a current flowing in the opposite direction, e.g., a negative current.

The operation of the dump circuits 95, 115 are similar to the electrode sites 100. If, for example, the use of a short dump circuit 95 is desired, switch A(short) may close so that $V_w$ from the DAC 30 may charge capacitor 90. When charged, the capacitor 90 supplies a voltage to the noninverting input terminal (+) of operational amplifier 140. The output of the operational amplifier 140 is fed back into the inverting input terminal (−) of the operation amplifier 140. Additionally, switches G and M may be closed so the voltage output of the operational amplifier 140 may be applied to the dump electrode $D_s$, which may be coupled with the desired electrode site(s) 100.

Similarly, if the use of the long dump circuit 115 is desired, switch A(long) may close so that $V_w$ from the DAC 30 may charge capacitor 110. When charged, the capacitor 110 supplies a voltage to the noninverting input terminal (+) of operational amplifier 150. The output of the operational amplifier 150 is fed back into the inverting input terminal (−) of the operational amplifier 150. Additionally, switches L and N may be closed so the voltage output of the operational amplifier 150 may be applied to the dump electrode $D_1$, which also may be coupled with the desired electrode site(s) 100.

As mentioned above, the control logic module 50 may control the state and the modes of operation of the electrode sites 100 individually. Further, the control logic module 50 may also control the dump circuits 95, 115 by controlling switches G, M, L, N, and H.

Turning now to methods of delivering electrical stimuli to the working electrodes W, there are preferably at least three methods: constant voltage, constant current, and voltage reference. The constant voltage method involves applying a desired constant voltage to the working electrode W. In contrast, the constant current method involves applying a desired constant current to the working electrode W.

The voltage reference method involves maintaining a user programmable offset between a working electrode W and a reference voltage source $V_{ref}$. The voltage source $V_{ref}$ may be coupled with the array 20 via a reference electrode R. FIG. 4 shows $V_{ref}$ coupled with a reference electrode R that is coupled with the long dump circuit 115 via switch H, however $V_{ref}$ may be coupled with the array at other locations, for example, with the short dump circuit 95. The voltage of the reference electrode R may be monitored using a sensor amplifier 135 (represented as $V_3$ in FIG. 4). Preferably, the reference electrode R is located in the flow cell (discussed in more detail below) that is formed in connection with the chip 10.

The array-based electronic chip 10 may also control the delivery method of the electrical stimuli to each working electrode W and the dump circuits 95, 115, individually or in selected groups. To control the delivery of the electrical stimuli, the chip 10, using the DAC 30, sets voltage $V_w$, which is coupled to the electrode sites 100 and the dump circuits. The DAC 30 retrieves the desired $V_w$ value from the dual port RAM 80 and the control logic module 50. For an array 20 that has 400 electrode sites 100, a short dump circuit 95, and a long dump circuit 115, the RAM 80 may have 402 bytes of data. Each byte corresponds to an electrode site 100 or a dump circuit 95, 115 and represents a specific voltage for $V_w$.

The chip 10 charges each electrode site 100 and dump circuit 95, 115 sequentially, controlled by the counter 65. The counter 65 specifies the byte (n) within the RAM 80 that the DAC retrieves to set $V_w$. While the DAC 30 is retrieving the voltage value and setting $V_w$, the control logic 50 reads the module counter 65 and sets the corresponding electrode site 100 or dump circuit 95, 115 into the sample state, i.e., the control logic module 50 closes switch A(n) for the corresponding electrode site (n) 100 or dump circuit 95, 115. When the corresponding capacitor(s) 70, 90, 110 charges, the control logic module 50 changes the electrode site (n) 100 or dump circuit 95, 115 to a hold state, i.e., opens switch A(n).

The module counter 65 then increments to the next byte within the RAM 80, i.e., (n+1), and the DAC 30 reads the voltage value in the next byte (n+1) to set $V_w$. While the DAC 30 is retrieving the voltage value of byte (n+1) and setting $V_w$, the control logic 50 reads the counter 65 and sets the next electrode site (n+1) 100 or dump circuit 95, 115 into the sample state, i.e., the control logic module 50 closes switch A(n+1). When capacitor 70, 90, 110 charges, then the control logic module 50 opens switch A(n+1).

This process is known as "refreshing" the electrodes, and the process cycles through the sample-and-hold circuits 102 and dump circuits 95, 115 sequentially during operation. Timing is critical because the refreshing process must be fast enough to maintain the desired charges on the capacitors, 70, 90, 110, before they deplete to undesirable levels, but each circuit must maintain a sample state long enough for the respective capacitor, 70, 90, 110, to charge to the desired level. Using a dual port RAM 80 allows the counter 65 and the DAC 30 to access the RAM 80 simultaneously, which improves the timing of the chip 10. Preferably, the DAC 30 and the counter 65 are driven by a clock signal of approximately 10 MHz.

When the delivers electrical stimuli to a particular working electrode W via the constant voltage method, the desired voltage is applied via $V_w$, as described above. The desired voltage may be either a single voltage value or a programmed series of different voltage values, such as positive and negative voltages values. To maintain the desired constant voltage, the control logic module 50 may set the electrode site 100 of the particular working electrode W to voltage measurement mode. Thus, the voltage of the working electrode $V_2$ may be monitored. The measurement at $V_2$ may be fed into the ADC 40 to convert the measurement into a digital value. The control logic module 50 may then retrieve the working electrode W voltage $V_2$ from the ADC 40 to compare with the desired constant voltage. If $V_2$ is too high or too low, then the control logic module 50 may accordingly adjust the value for $V_w$ set in the RAM 80 for the corresponding electrode site 100.

When the chip 10 delivers electrical stimuli via the constant current method, the desired voltage Vw is applied to produce the desired constant current through the working electrode W, as described above. The desired constant current may be either a single value or a programmed series of different current values, such as positive and negative current values. To maintain the constant current, the control logic module 50 sets the corresponding electrode site 100 to current measurement mode and then monitors the current by retrieving data, such as $V_1$ and/or $V_2$, from the ADC 40 and calculating the current, as described above. If the current is too high or too low, the control logic 50 may accordingly adjust the $V_w$.

When the chip 10 delivers electrical stimuli via the voltage reference method, the desired $V_w$ is applied such that the voltage at the working electrode W is offset from $V_{ref}$ by a user programmable amount. The programmed offset may be either a single value or a series of different values, such as positive and negative values. To maintain the user programmable offset, the control logic module 50 sets the particular electrode site 100 to dry voltage test mode and then compares $V_2$ with $V_3$, the voltage of the reference electrode R that is coupled with $V_{ref}$. If the offset is too much or too little, the control logic module 50 may accordingly adjust $V_w$, as described above.

The control logic module 50 also includes a reset signal, which, when invoked, refreshes the electrodes sites 100 and the dump circuits 95, 115 starting from the first electrode site 100, i.e., the counter 65 is reset to 0.

In addition, the control logic module 50 may monitor the temperature of the array 20 via the temperature sensor module 139.

As mentioned above, the chip 10 further includes an EEPROM 90 coupled with the control logic module 50. This allows the control logic module 50 to store extra data associated with the array 20, e.g., calibration data for the temperature sensor 139. The EEPROM 90 is read/write, but the data may be changed by "powering up" the EEPROM 90 only. This may be achieved by applying approximately 20V to $V_{pp}$ and performing a write.

Turning now to a description of the interface with the chip 10 and more specifically with the control logic module 50, the interface is a three wire serial interface which includes data-in 52, data-out 53, and clock 51, as shown in FIG. 3. Although data-in 52 and data-out 53 are separate, the interface is half duplex, i.e., a response coming from the chip 10 occurs only after a command from the external processor 62 has been fully received. The interface is synchronously driven by the clock 51, preferably at 10 MHz. Preferably, there is a two clock cycle delay between data-in 52 and data-out 53. The data-in 52 signal is a 24-bit message which includes: a start bit, a 12-bit address, a 1-bit command, an 8 bit data field, and two stop bits.

The 12-bit address may represent, for example, the individual switches controls, A, B, C, D, E, G, M, L, N, H, the DAC 30 controls, the data to be written to either the EEPROM 90 or the RAM 80, e.g., voltage values for $V_w$ when the DAC 30 refreshes the electrode sites 100, the ADC 40 controls, temperature sensor 139 controls.

The 1-bit command may indicate whether the external processor 62 intends to read data from the chip 10 or write data to the chip 10, e.g., write to the RAM 80 or EEPROM 90 or control the switches.

The data-out signal is an 11-bit message produced by the control logic module 50 if the 1-bit command in data-in is a read command. The data-out signal includes: a start bit, an 8-bit data field, and two stop bits. The 8-bit data field may include, for example, the status of the switches, i.e., whether the switch is open or closed and/or data from the RAM 80, EEPROM 90, and/or ADC 40, which may include data from $V_1$, $V_2$, $V_3$, $V_{ref}$, and/or T.

Figure 6:
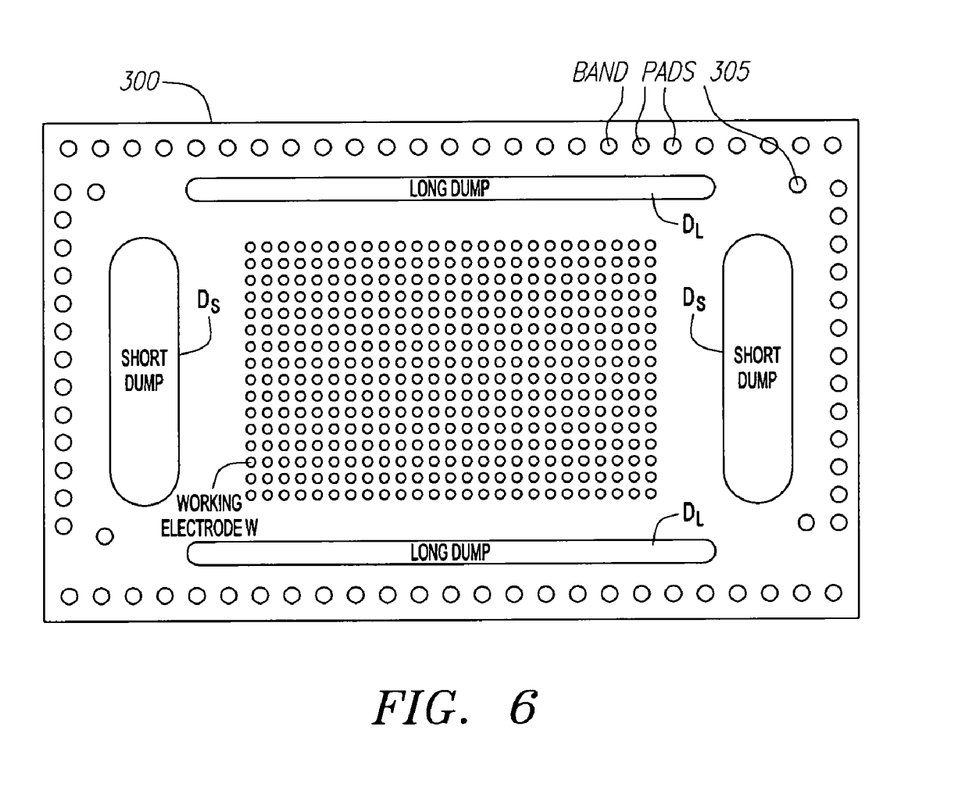
FIG. 6 is an illustration of a die layout of an array-based circuit in accordance with a preferred embodiment of the present invention.

Turning to FIG. 6, a preferred die 300 layout of an embodiment of the present invention is shown. The die 300 is preferably approximately 8 mm by 5 mm. 400 working electrodes W of the array 20 are shown in a matrix of 16 rows and 25 columns. However, an embodiment of the present invention may include any number of working electrodes W. The electrodes W are preferably approximately 50 microns in diameter on 150 micron centers. In addition, the working electrodes W are preferably comprised of platinum or platinum silicide and are preferably planar.

The long dump electrodes $D_l$ and the short dump electrodes $D_s$ are also shown along the perimeter of the working electrodes W. Around the perimeter of the layout are bond pads 305 for chip related functions. It should be noted that in this particular layout, the reference electrode R is not shown. In a preferred form, the reference electrode is comprised of silver, and thus resides off the die 300, preferably in the flow cell 230. The reference electrode R may be coupled to the array 20 via the bond pads. The remaining elements of the chip 10 reside within the die 300.

Preferably, the chip 10 may be designed such that there is less than 10% electrode current variation from 630 nm light incident at 10 mw/mm$^2$. An optical block (not shown) may be placed in the top of the metallization layer of the electrodes W to help resolve this issue. Optionally, there may be four electrode size areas (not shown) in between the dump circuits 95, 115 and the array of electrode sites 100 towards the corner of the die 300 coated with a fluorescent material to be used as an optical standard.

Figure 7A:
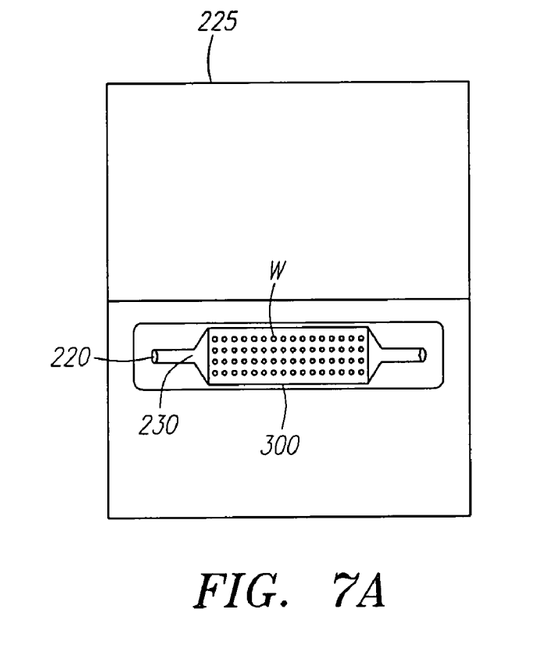

Turning to FIG. 7(a), the die 300 is shown installed in a cartridge 225 used to apply a solution to the working electrodes W and more readily couple the chip 10 with an external processor 62. The cartridge 225 includes a flow cell 230 that acts as a chamber over the die 300 that contains the solution containing charged biological material. Injection ports 220 are placed on both sides of the die 300. The solution enters one port 220, flows over the working electrodes W, and exits the other port 220.

Figure 7B:
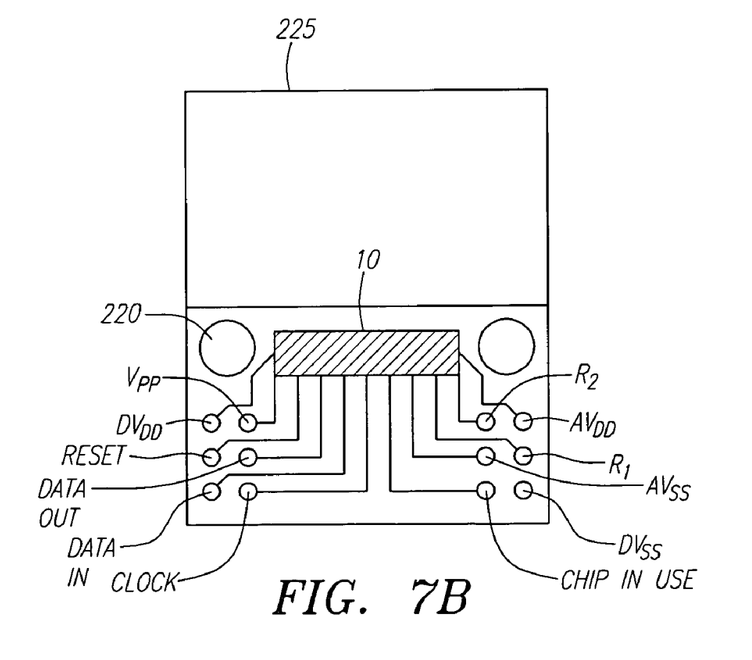

Turning to FIG. 7(b), the flip-side of the cartridge 225 and the die 300 is shown. The cartridge 225 further includes pins within the die 300 to electrically connect certain elements within the array-based chip 10 to external components. The $V_{pp}$ pin is for coupling a power supply of approximately 20V with the EEPROM 90. The $D_{Vdd}$ pin is for coupling the array-based chip 10 with a digital power supply of approximately 5V, and the $A_{Vdd}$ pin is for coupling the chip 10 with an analog power supply of approximately 5V. The Reset pin is for coupling a reset signal to the control logic module 50.

The data-out 53, data-in 52, and clock 51 pins are for interfacing with the external processor 62, which may be via a transceiver 60. The $R_1$ and $R_2$ pins are for coupling each end of an external resistor, e.g., resistor 130, to the array 20. The $A_{Vss}$ pin is for coupling the array 20 with an analog ground, and the $D_{Vss}$ is for coupling the array 20 with a digital ground. A chip-is-in-use pin provides a signal that indicates whether the chip 10 is in operation.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. A digitally programmable array-based electronic chip for carrying out biological reactions in response to electrical stimuli, comprising:
    an array of electrode sites, each electrode site including a sample-and-hold circuit coupled to a working electrode;
    a plurality of switches for selectively coupling the working electrodes to the output of a digital-to-analog converter (DAC);
    a control logic module coupled to the DAC and the plurality of switches;
    a measurement circuit comprising one or more electrical output pathways for selectively coupling the array of electrode sites to an analog-to-digital converter (ADC), the ADC coupled to the control logic module;
    a current measurement circuit, the current measurement circuit comprising a first selectable connection to the sample-and-hold circuit, a series connected resistor and a second selectable connection to the sample-and-hold circuit, the current measurement circuit operating in a current measurement mode when the first and second selectable connections are closed and in a high impedance mode when the first and second selectable connections are open; and
    an external processor that digitally interfaces with the control logic module, wherein the communication between the control logic and the external processor includes a clock signal, a data in signal, and a data out signal.

2. The electronic chip of claim 1, wherein the sample-and-hold circuits may be configured to operate in normal mode, current measurement mode, high-impedance mode, and voltage measurement mode.

3. The electronic chip of claim 1, further comprising a temperature sensor.

4. The electronic chip of claim 1, further comprising a transceiver coupled with the control logic module for enabling the external processor to communicate with the control logic module through a serial interface.

5. The electronic chip of claim 1, further comprising:
    a dual port random access memory module, having a plurality of addresses, coupled to the DAC and the control logic module; and
    a counter coupled to the dual port random access memory; wherein the DAC retrieves a value from the memory to produce a corresponding voltage and the counter specifies the address within the memory where the DAC retrieves the value.

6. The electronic chip of claim 1, further comprising a measurement circuit coupled with the array, configured for measuring the voltage and current through the electrodes.

7. The electronic circuit of claim 1, further comprising a reference electrode coupled with the array and an external voltage source coupled with the reference electrode.

8. The electronic chip of claim 1, wherein the measurement circuit is capable of measuring temperature.

9. A method for carrying out biological reactions in response to electrical stimuli applied to a plurality of electrodes, comprising the steps of:
    providing a chip having an array of electrode sites, each electrode site containing a sample-and-hold circuit coupled to a working electrode, a digital-to-analog converter (DAC), a plurality of switches for selectively coupling the DAC to the working electrodes, and a control logic module coupled to the DAC and the plurality of switches; providing an external processor that digitally interfaces with the chip;
    providing a measurement circuit comprising one or more electrical output pathways for selectively coupling the array of electrodes to an analog-to-digital converter (ADC), the ADC coupled to the control logic module;
    providing a current measurement circuit, the current measurement circuit comprising a first selectable connection to the sample-and-hold circuit, a series connected resistor and a second selectable connection to the sample-and-hold circuit, the current measurement circuit operating in a current measurement mode when the first and second selectable connections are closed and in a high impedance mode when the first and second selectable connections are open; and
    driving the working electrodes in accordance with instructions contained in the external processor.

10. The method of claim 9, wherein the external processor interfaces with the chip using a transceiver, the transceiver communicating with the chip using a data in signal, a data out signal, and a clock signal.

11. The method of claim 9, wherein the working electrodes are driven at a constant voltage.

12. The method of claim 9, wherein the working electrodes are driven at a constant current.

13. The method of claim 9, wherein the working electrodes are driven at a voltage that is offset from a reference voltage.

14. The method of claim 9, further comprising the step of providing a temperature sensor adjacent to the chip and measuring the temperature of a solution contained on the chip.

15. The method of claim 9, further comprising the step of measuring the current running through an individual electrode or a selected group of electrodes.

16. The method of claim 9, further comprising the step of measuring the voltage running through an individual electrode or a selected group of electrodes.

17. The method of claim 13, further comprising the step of monitoring a user programmable offset between the reference voltage and the voltage of an individual electrode or a selected group of electrodes.

18. The method of claim 9, further comprising the step of sequentially refreshing the sample-and-hold circuits.

19. The method of claim 18, wherein the sample-and-hold circuits are refreshed synchronously with a clock signal having a frequency of approximately 10 MHz.

20. The method of claim 18, wherein the sample-and-hold circuits are refreshed using the DAC, and wherein the DAC is coupled to a dual port random access memory that is further coupled to a counter.

21. The electronic chip of claim 1, wherein the measurement circuit is capable of measuring voltage.

22. The electronic chip of claim 21, wherein the measurement circuit further comprises an external resistor and two nodes coupled with two voltage sense amplifiers.

* * * * *